(12) United States Patent
Burroughs, III

(10) Patent No.: US 11,376,022 B2
(45) Date of Patent: Jul. 5, 2022

(54) PATELLA CUTTING GUIDE

(71) Applicant: Quadvantage Technology, Inc., Raleigh, NC (US)

(72) Inventor: Paul Leach Burroughs, III, Raleigh, NC (US)

(73) Assignee: Quadvantage Technology, Inc., Raleigh, NC (US)

( * ) Notice: Subject to any disclaimer, the term of this patent is extended or adjusted under 35 U.S.C. 154(b) by 207 days.

(21) Appl. No.: 16/515,859

(22) Filed: Jul. 18, 2019

(65) Prior Publication Data

US 2021/0015497 A1   Jan. 21, 2021

(51) Int. Cl.
| | | |
|---|---|---|
| *A61B 17/16* | (2006.01) | |
| *A61B 17/17* | (2006.01) | |
| *A61B 90/00* | (2016.01) | |

(52) U.S. Cl.
CPC ...... *A61B 17/1677* (2013.01); *A61B 17/1767* (2013.01); *A61B 2090/033* (2016.02)

(58) Field of Classification Search
CPC ................... A61B 17/1677; A61B 17/1767
See application file for complete search history.

(56) References Cited

U.S. PATENT DOCUMENTS

| | | | |
|---|---|---|---|
| 622,461 | A | 4/1899 | Glardon-Jaquet et al. |
| 1,830,692 | A | 11/1931 | Becker |
| 3,452,754 | A | 7/1969 | Stayer |
| 3,583,390 | A | 6/1971 | Jascalevich |
| 3,815,604 | A | 6/1974 | O'Malley et al. |
| 3,844,272 | A | 10/1974 | Banko |
| 3,902,498 | A | 9/1975 | Niederer |
| 4,099,529 | A | 7/1978 | Peyman |
| 4,106,620 | A | 8/1978 | Brimmer et al. |
| 4,120,397 | A | 10/1978 | Neumann |
| 4,185,634 | A | 1/1980 | Freedman |
| 4,341,305 | A | 7/1982 | Schultz |

(Continued)

FOREIGN PATENT DOCUMENTS

| | | |
|---|---|---|
| CN | 107714158 A | 2/2018 |
| DE | 8903079 U1 | 5/1989 |

(Continued)

OTHER PUBLICATIONS

Author Unknown, "New or Refurbished—ValleyLab Force FX," DRE INC, accessed on May 6, 2011, www.dremed.com/catalog/product_info.php/cPath/45_78/products_id/421, 1 page.

(Continued)

*Primary Examiner* — Matthew J Lawson
(74) *Attorney, Agent, or Firm* — Withrow & Terranova, PLLC

(57) ABSTRACT

A guide is disclosed that operates to guide in the creation of a bone spur to facilitate harvesting a quadriceps tendon and includes an end having a width equal to a desired graft width with a terminal slope equal to a cutting angle desired. In use, the guide may be initially positioned parallel to the femur to form guide cuts in the patella. The guide is then rotated ninety degrees to allow an angled cut at the guide cut. The guide is again rotated, this time one hundred eighty degrees and a second angled cut made on the other guide cut. A final lateral cut is made and the bone spur may be lifted from the patella.

10 Claims, 13 Drawing Sheets

(56) References Cited

U.S. PATENT DOCUMENTS

| | | |
|---|---|---|
| 4,461,305 A | 7/1984 | Cibley |
| 4,578,865 A | 4/1986 | Keller |
| 4,696,298 A | 9/1987 | Higgins et al. |
| 4,746,016 A | 5/1988 | Pollak et al. |
| 4,773,417 A | 9/1988 | Moore et al. |
| 4,832,045 A | 5/1989 | Goldberger |
| 4,985,031 A | 1/1991 | Buss et al. |
| 5,007,917 A | 4/1991 | Evans |
| 5,026,385 A | 6/1991 | Schutte et al. |
| 5,100,391 A | 3/1992 | Schutte et al. |
| 5,112,299 A | 5/1992 | Pascaloff |
| 5,217,463 A | 6/1993 | Mikhail |
| 5,226,910 A | 7/1993 | Kajiyama et al. |
| 5,250,050 A | 10/1993 | Poggie et al. |
| 5,267,572 A | 12/1993 | Bucalo |
| 5,269,798 A | 12/1993 | Winkler |
| 5,285,795 A | 2/1994 | Ryan et al. |
| 5,346,497 A | 9/1994 | Simon et al. |
| 5,391,169 A | 2/1995 | McGuire |
| 5,447,516 A | 9/1995 | Gardner |
| 5,496,325 A | 3/1996 | McLees |
| 5,505,210 A | 4/1996 | Clement |
| 5,507,762 A | 4/1996 | Abidin et al. |
| 5,528,811 A | 6/1996 | Abidin et al. |
| 5,549,618 A | 8/1996 | Fleenor et al. |
| 5,570,700 A | 11/1996 | Vogeler |
| 5,630,826 A | 5/1997 | Sastri |
| 5,720,760 A | 2/1998 | Becker et al. |
| 5,722,977 A | 3/1998 | Wilhelmy |
| 5,807,277 A | 9/1998 | Swaim |
| 5,893,862 A | 4/1999 | Pratt et al. |
| 5,911,730 A | 6/1999 | McGuire |
| 5,919,201 A | 7/1999 | Carter et al. |
| 5,933,968 A | 8/1999 | Solomon |
| 5,938,027 A | 8/1999 | Soroff et al. |
| 6,007,537 A * | 12/1999 | Burkinshaw ......... A61B 17/155 606/66 |
| 6,030,400 A | 2/2000 | Johnson |
| 6,033,375 A | 3/2000 | Brumbach |
| 6,035,536 A | 3/2000 | Dewberry |
| 6,053,928 A | 4/2000 | Van Wyk et al. |
| 6,217,599 B1 | 4/2001 | McGuire |
| 6,258,094 B1 | 7/2001 | Nicholson et al. |
| 6,391,031 B1 | 5/2002 | Toomey |
| 6,416,524 B1 | 7/2002 | Critz et al. |
| 6,500,187 B1 | 12/2002 | Petersen |
| 7,163,547 B2 | 1/2007 | Majlessi |
| 7,285,122 B2 | 10/2007 | Sanford et al. |
| 7,320,687 B2 | 1/2008 | Lee |
| 7,346,989 B2 | 3/2008 | Shi |
| 7,398,880 B2 | 7/2008 | Henry |
| 7,901,404 B2 | 3/2011 | Reay-Young |
| 8,308,746 B2 | 11/2012 | Pravong et al. |
| 8,430,896 B2 | 4/2013 | Murakami et al. |
| D685,089 S | 6/2013 | Yaremchuk et al. |
| 8,454,610 B2 | 6/2013 | Skaggs |
| 8,545,485 B2 | 10/2013 | Merced-O'Neill |
| 8,551,101 B2 | 10/2013 | Kuczynski |
| 8,567,072 B2 | 10/2013 | Yi et al. |
| 8,894,672 B2 | 11/2014 | Burroughs, III |
| 8,894,675 B2 | 11/2014 | Burroughs, III |
| 8,894,676 B2 | 11/2014 | Burroughs, III |
| 8,931,181 B2 | 1/2015 | Milton et al. |
| 9,044,260 B2 | 6/2015 | Burroughs, III |
| 9,101,388 B2 | 8/2015 | Yi et al. |
| 9,107,700 B2 | 8/2015 | Burroughs, III |
| 9,474,535 B2 | 10/2016 | Burroughs, III |
| 10,064,647 B2 | 9/2018 | Severns et al. |
| 2001/0039429 A1 | 11/2001 | McGuire |
| 2004/0102772 A1 | 5/2004 | Baxter et al. |
| 2005/0090829 A1* | 4/2005 | Martz ................ A61B 17/1604 606/79 |
| 2005/0137704 A1 | 6/2005 | Steenlage |
| 2005/0149092 A1 | 7/2005 | Dunn |
| 2005/0228393 A1* | 10/2005 | Williams, III ....... A61B 17/155 606/87 |
| 2006/0004397 A1 | 1/2006 | Osawa |
| 2006/0111722 A1 | 5/2006 | Bouadi |
| 2006/0212057 A1 | 9/2006 | Djordjevic et al. |
| 2006/0212059 A1 | 9/2006 | Booth |
| 2006/0212060 A1 | 9/2006 | Hacker et al. |
| 2007/0288055 A1 | 12/2007 | Lee |
| 2008/0021487 A1 | 1/2008 | Heisler |
| 2008/0065113 A1 | 3/2008 | Smith |
| 2008/0161810 A1 | 7/2008 | Melkent |
| 2008/0221569 A1* | 9/2008 | Moore ............... A61B 17/1767 606/53 |
| 2008/0306483 A1 | 12/2008 | Iannarone |
| 2009/0048485 A1 | 2/2009 | Heisler |
| 2010/0069944 A1 | 3/2010 | Murakami et al. |
| 2011/0004214 A1 | 1/2011 | Skaggs |
| 2011/0087260 A1 | 4/2011 | Seipel et al. |
| 2011/0106122 A1 | 5/2011 | Cetola |
| 2012/0059247 A1 | 3/2012 | Speeg et al. |
| 2012/0065658 A1 | 3/2012 | Heisler |
| 2012/0191121 A1 | 7/2012 | Chen et al. |
| 2013/0079787 A1* | 3/2013 | Spencer Jones ... A61B 17/1767 606/96 |
| 2013/0079788 A1* | 3/2013 | Spencer Jones ... A61B 17/1767 606/96 |
| 2014/0257300 A1* | 9/2014 | Christie ............... A61B 17/155 606/83 |
| 2014/0277020 A1 | 9/2014 | Koogle et al. |
| 2016/0120560 A1 | 5/2016 | Burroughs, III |
| 2016/0128712 A1 | 5/2016 | Ruggiero, Sr. |
| 2017/0100151 A1 | 4/2017 | Severns et al. |
| 2017/0135716 A1 | 5/2017 | Endo |

FOREIGN PATENT DOCUMENTS

| | | | |
|---|---|---|---|
| EP | 2438866 A1 | 4/2012 | |
| FR | 2665628 A1 | 2/1992 | |
| FR | 2737848 A1 * | 2/1997 | ......... A61B 17/1767 |
| JP | H11-347039 A | 12/1999 | |
| JP | 2010284478 A | 12/2010 | |
| WO | 2008019097 A2 | 2/2008 | |
| WO | 2008093747 A1 | 8/2008 | |
| WO | 2010065508 A1 | 6/2010 | |

OTHER PUBLICATIONS

Author Unknown, "Cautery Electrodes," DRE INC, accessed on May 6, 2011, www.orsupply.com/medical/category/Cautery+Electrodes/489, 3 pages.

Extended European Search Report for European Patent Application No. 12782646.9, dated Dec. 17, 2014, 8 pages.

Notice of Grounds for Rejection for Japanese Patent Application No. 2014-510388, dated Mar. 22, 2016, 12 pages.

First Official Office Action for Mexican Patent Application No. MX/a/2013/012853, dated May 4, 2016, 4 pages.

International Search Report and Written Opinion for PCT/US2012/036728, dated Nov. 23, 2012, 10 pages.

International Preliminary Report on Patentability for PCT/US2012/036728, dated Nov. 21, 2013, 6 pages.

International Search Report and Written Opinion for PCT/US2013/044973, dated Sep. 5, 2013, 12 pages.

International Preliminary Report on Patentability for PCT/US13/44973, dated Jun. 4, 2014, 6 pages.

Non-Final Office Action for U.S. Appl. No. 13/102,562, dated Oct. 15, 2013, 14 pages.

Final Office Action for U.S. Appl. No. 13/102,562, dated May 8, 2014, 13 pages.

Applicant-Initiated Interview Summary for U.S. Appl. No. 13/102,562, dated Jul. 1, 2014, 3 pages.

Advisory Action for U.S. Appl. No. 13/102,562 dated, Jul. 22, 2014, 3 pages.

Notice of Allowance for U.S. Appl. No. 14/529,262, dated Mar. 27, 2015, 8 pages.

(56) References Cited

OTHER PUBLICATIONS

Non-Final Office Action for U.S. Appl. No. 14/753,197, dated Jan. 13, 2016, 8 pages.
Notice of Allowance and Exmainer-Initiated Interview Summary for U.S. Appl. No. 14/753,197, dated Jul. 7, 2016, 8 pages.
Non-Final Office Action for U.S. Appl. No. 13/493,320, dated Dec. 23, 2013, 7 pages.
Final Office Action for U.S. Appl. No. 13/493,320, dated May 15, 2014, 8 pages.
Advisory Action for U.S. Appl. No. 13/493,320, dated Jul. 17, 2014, 3 pages.
Notice of Allowance for U.S. Appl. No. 13/493,320, dated Aug. 25, 2014, 7 pages.
Non-Final Office Action for U.S. Appl. No. 13/832,638, dated May 30, 2014, 8 pages.
Notice of Allowance for U.S. Appl. No. 13/832,638, dated Aug. 21, 2014, 7 pages.
Notice of Allowance for U.S. Appl. No. 14/529,309, dated Jan. 26, 2015, 11 pages.
International Search Report and Written Opinion for International Patent Application No. PCT/US2020/037508, dated Sep. 9, 2020, 16 pages.
International Search Report and Written Opinion for International Patent Application No. PCT/US2020/042482, dated Oct. 5, 2020, 17 pages.
Author Unknown, "Minimally Invasive Quadriceps Tendon Harvesting System," EndoWorld, Art 52, 4.0, Nov. 2015, Karl Storz Endoscopy-America, Inc., 12 pages.
Office Action for Brazilian Patent Application No. BR112013028474-9, dated Jul. 21, 2020, 5 pages.
Author Unknown, "SPEC Coatings," Product Specification, available at least as early as Apr. 9, 2021, United Protective Technologies, Locust, NC, 1 page.
Written Opinion for International Patent Application No. PCT/US2020/042482, dated Jun. 22, 2021, 5 pages.
Non-Final Office Action for U.S. Appl. No. 16/900,315, dated Jul. 15, 2021, 10 pages.

\* cited by examiner

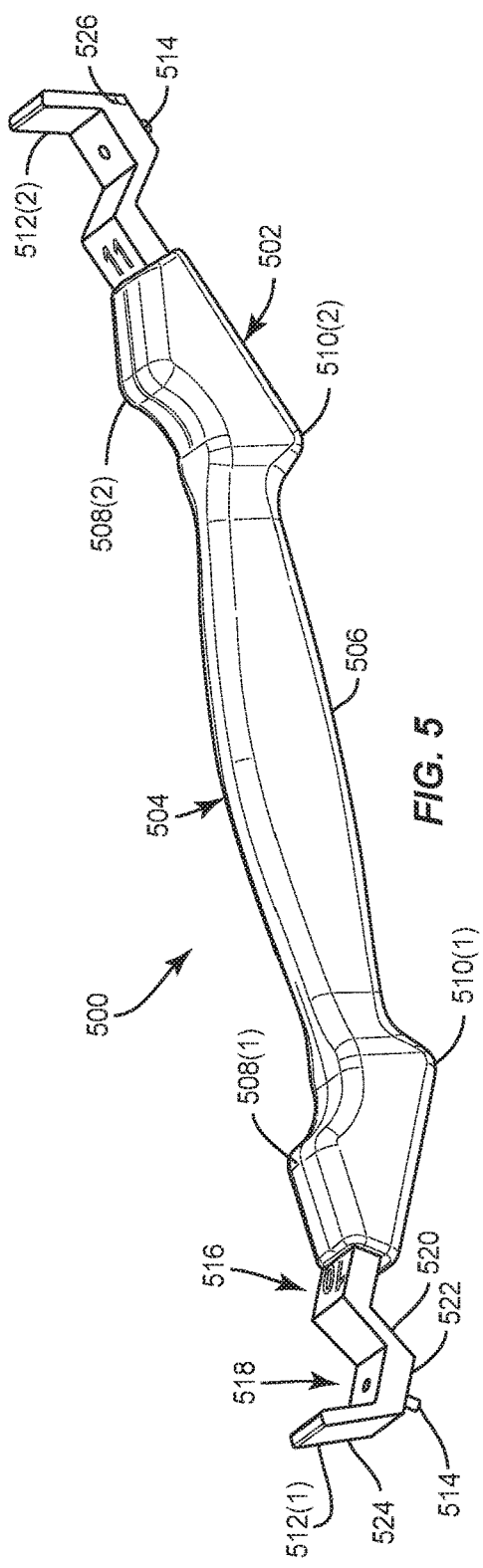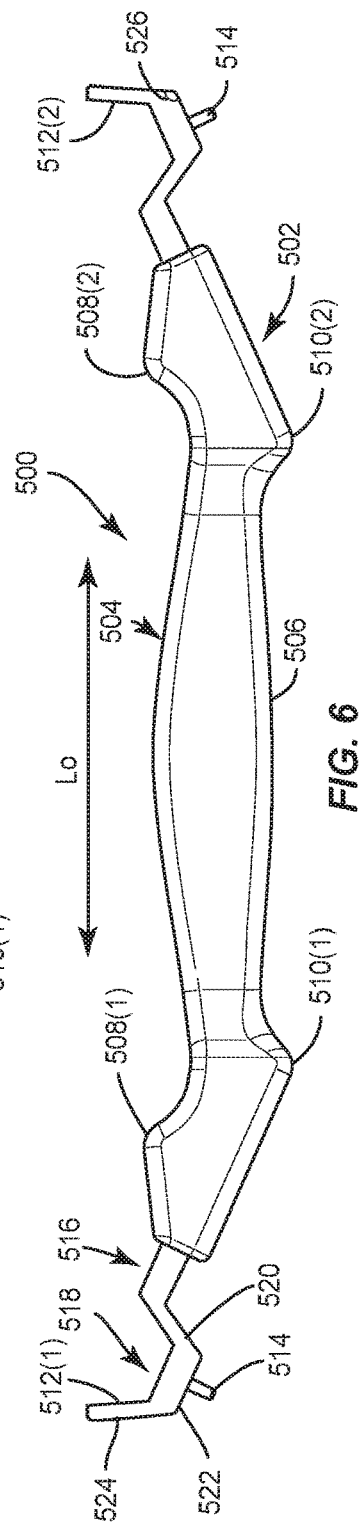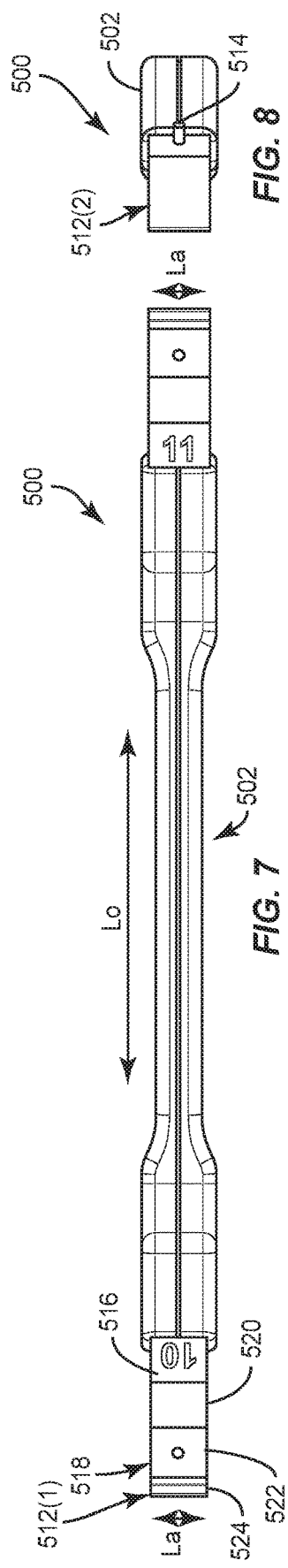

PATELLA CUTTING GUIDE

FIELD OF THE DISCLOSURE

The present disclosure relates to a guide that is used to create a bone spur or plug from a patella bone during quadriceps tendon harvesting.

BACKGROUND

Most people can go through the majority of their life without ever caring or knowing how complicated a structure the knee that helps them walk is. However, the knee remains a fragile mechanical structure that is readily susceptible to damage. While medical advances have made repairing the knee possible, repair of certain types of injuries results in other long term effects. To assist the reader in appreciating the elegance of the present disclosure, FIG. 1 is provided with a brief explanation of the components of the knee.

For the purposes of the present disclosure, and as illustrated, the knee may be composed of the quadriceps muscles 100, the femur 102, the articular cartilage 104, the lateral condyle 106, the posterior cruciate ligament 108, the anterior cruciate ligament 110, the lateral collateral ligament 112, the fibula 114, the tibia 116, the patellar tendon 118, the meniscus 120, the medial collateral ligament 122, the patella 124 (shown slightly displaced to the side—it normally rests in the center of the knee), and the quadriceps tendon 126. Of particular interest for the purposes of the present disclosure is the anterior cruciate ligament (ACL) 110 and what is done to repair the ACL 110.

ACL tears are common in athletes and are usually season-ending injuries. The ACL 110 cannot heal—it must be surgically reconstructed. The reconstruction requires replacement tissue. The most common tissue used is a central slip of the patient's own patellar tendon 118. In practice, the patellar tendon 118 has proven to be generally effective, but the size of the graft that can be used is limited to the size of the patient's own patellar tendon 118. As a rule of thumb, only a third of the patellar tendon 118 may be harvested as a graft. Thus, a doctor will measure the width of the patellar tendon 118, divide by three, and take the middle third of the patellar tendon 118. Such harvested grafts are rarely more than ten millimeters (10 mm) wide and may be smaller. Taking this tissue from a person's patellar tendon 118 also causes significant pain and discomfort in the post-operative healing period, which may last up to a year, and up to twenty (20) percent of these patients are left with chronic anterior knee pain.

Some doctors recommend and use other graft sources, such as cadaver grafts, but cadaver grafts have a higher failure rate. Additionally, there is a non-zero chance of disease transmission or rejection by the patient's immune system. As a final drawback, cadaver grafts are usually quite expensive and may not be covered by some insurance companies.

Other doctors use hamstring tendons (e.g., the distal semitendinosus tendon) because the scar created during harvesting is relatively small and there is less pain during the rehabilitation, but again, the hamstring tendon has its own collection of disadvantages. The disadvantages include the fact that once the graft is taken, a patient's hamstring will never recover to its previous strength. Further, all hamstring reconstructions stretch and are looser than the original ACL 110. This loosening is particularly problematic in younger female athletes.

Another alternative graft source is the quadriceps tendon 126. The quadriceps tendon 126 is larger and stronger than either the patellar tendon 118 or the hamstring tendon. The quadriceps tendon 126 is likewise stiffer and less prone to stretching or plastic deformation. However, the qualities that make the quadriceps tendon 126 attractive also contribute to the difficulty in harvesting a graft from the quadriceps tendon 126. Existing surgical implements require a large incision up the longitudinal axis of the femur 102 on the front or ventral/anterior side of the thigh to cut down to the level of the quadriceps tendon 126, resulting in a large post-operative scar. Additionally, the quadriceps tendon 126 has a consistency similar to the proverbial shoe leather, making it difficult to cut. However, an ACL 110 repaired with grafts from the quadriceps tendon 126 generally result in almost no anterior knee pain postoperatively over the short or long term and patients recover quicker.

U.S. Pat. Nos. 8,894,672; 8,894,675; 8,894,676; 9,044,260; 9,107,700; and 9,474,535 provide a number of devices designed to create a graft from the quadriceps tendon 126 well as a number of secondary cutting implements to trim the distal end of the graft. While these cutting implements are adequate to perform their intended purpose, creating the initial bone spur from the patella to which the quadriceps tendon is attached may still be a challenge.

SUMMARY

The present disclosure provides a guide device that operates to guide in the creation of a bone spur to facilitate harvesting a quadriceps tendon. In an exemplary aspect, the cutting guide includes an end having a width equal to a desired graft width with a terminal slope equal to a cutting angle desired. In use, the guide may be initially positioned parallel to the femur to form guide cuts in the patella. The guide is then rotated ninety degrees to allow an angled cut at the guide cut. The guide is again rotated, this time one hundred eighty degrees and a second angled cut made on the other guide cut. A final lateral cut is made and the bone spur may be lifted from the patella. The use of such a guide facilitates creation of a properly sized bone spur, which in turn creates a properly sized graft.

In this regard, in one aspect, a cutting guide is disclosed. The cutting guide includes a handle portion. The cutting guide also includes a terminal portion extending from the handle portion. The terminal portion includes a flat portion having a bottom side and a corner. The terminal portion also includes a post extending from the bottom side. The terminal portion also includes an upwardly sloping wall extending from the corner.

In another aspect, a method of cutting a workpiece is disclosed. The method includes placing a cutting guide against the workpiece. The method also includes cutting at least one guide line on a side of the cutting guide. The method also includes rotating the cutting guide ninety degrees. The method also includes cutting an angled cut using an upwardly sloped wall of the cutting guide.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure, and together with the description serve to explain the principles of the disclosure.

FIG. 5 illustrates a perspective view of a cutting guide according to an exemplary aspect of the present disclosure;

FIG. 6 illustrates a top view of the cutting guide of FIG. 5;

FIG. 7 illustrates a side view of the cutting guide of FIG. 5;

FIG. 8 illustrates an end view of the cutting guide of FIG. 5;

DETAILED DESCRIPTION

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

The present disclosure provides a guide device that operates to guide in the creation of a bone spur to facilitate harvesting a quadriceps tendon. In an exemplary aspect, the cutting guide includes an end having a width equal to a desired graft width with a terminal slope equal to a cutting angle desired. In use, the guide may be initially positioned parallel to the femur to form guide cuts in the patella. The guide is then rotated ninety degrees to allow an angled cut at the guide cut. The guide is again rotated, this time one hundred eighty degrees and a second angled cut made on the other guide cut. A final lateral cut is made and the bone spur may be lifted from the patella. The use of such a guide facilitates creation of a properly sized bone spur, which in turn creates a properly sized graft.

Before addressing the particular structure of the guide, a brief overview of the process that harvests a quadriceps tendon is provided. A discussion of the guide of the present disclosure begins below with reference to FIG. 5.

Figure 1:
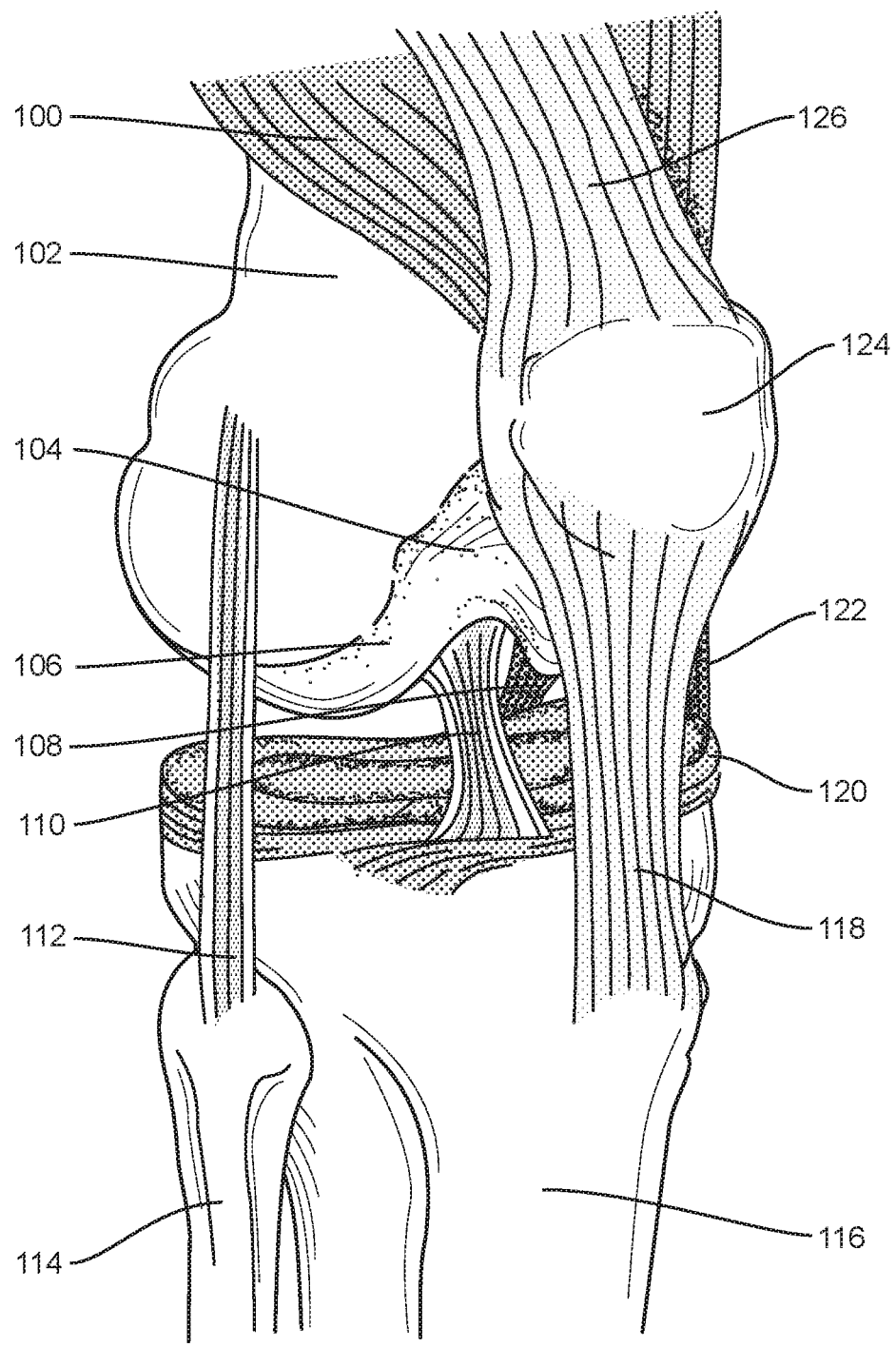
FIG. 1 illustrates a conventional knee.
Figure 2:
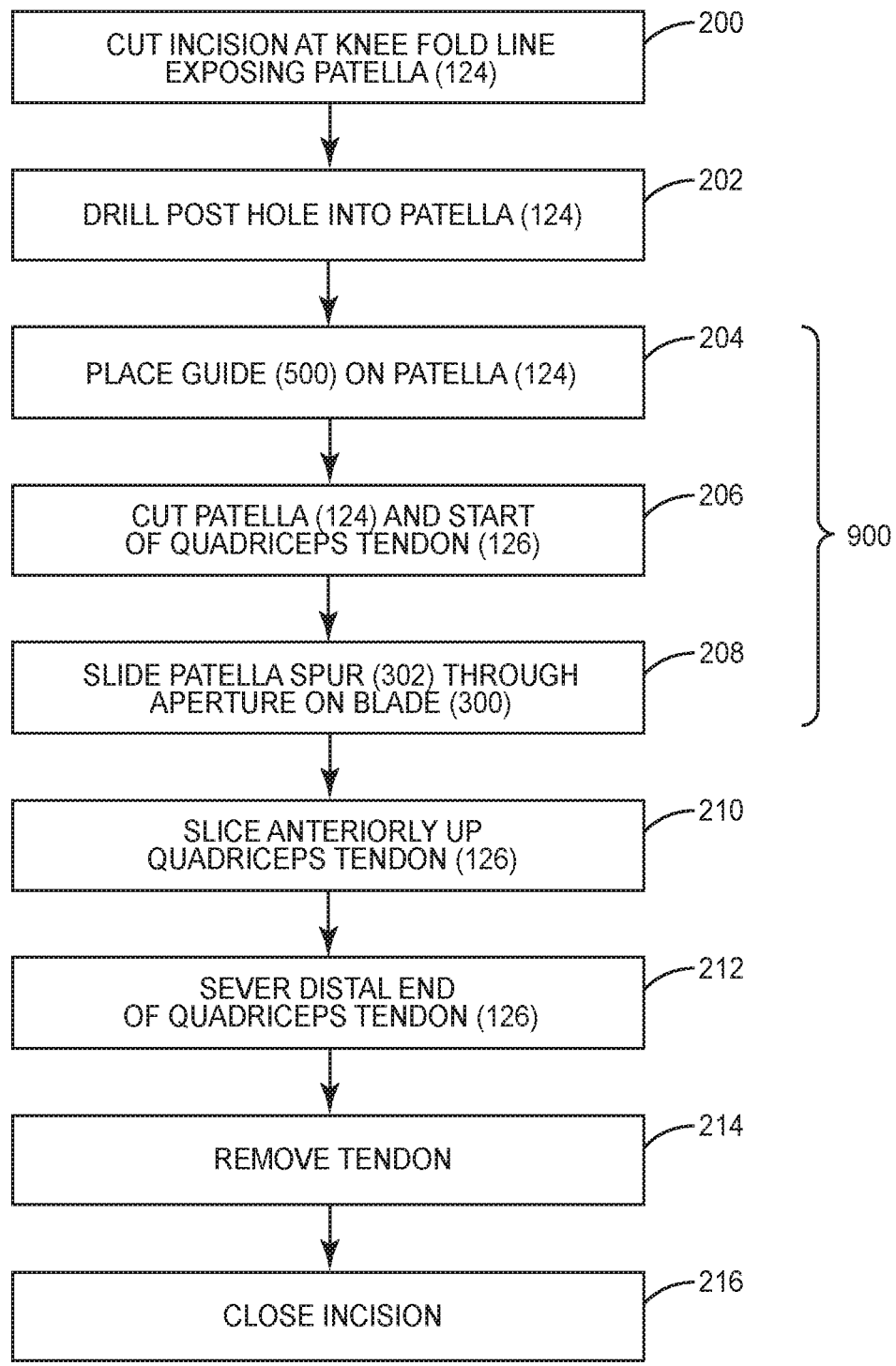
FIG. 2 illustrates a flowchart describing the process of harvesting a quadriceps tendon.

FIG. 2 illustrates a flowchart explaining how a tendon graft is harvested. The doctor makes or cuts an initial incision at a knee fold line (block 200), such as an anterior fold line, and folds the skin back to expose a portion of the patella 124. The doctor drills a post hole into the patella 124 proximate the quadriceps tendon 126 (block 202). The hole may be approximately eleven millimeters (11 mm) deep or sufficiently deep to pass through the patella 124. The doctor then places the guide 500 (see FIG. 5 below) on the patella 124, with the post positioned within the hole (block 204). The doctor will chose the width of the quadriceps tendon 126 to be harvested by measuring the size of the quadriceps tendon 126 preoperatively from MRI imaging and comparing the images to the intraoperative observations of the tendon itself. A cross-sectional area of the patellar tendon can be calculated from the MRI, and one third of this patellar tendon area can be compared to the cross-sectional areas resulting from different quadriceps options.

Next, a bone plug or spur 302 (see FIG. 3 below) is created by cutting into the patella 124 using the sidewalls of the guide 500 to guide the cuts into the patella 124, thereby creating the bone plug 302 and the initial cut into the quadriceps tendon 126 (block 206). As explained in greater detail below, the guide 500 directs the saw blade such that the resulting bone plug 302 is of the same lateral dimensions as the quadriceps graft that has been chosen, allowing the bone spur to be slipped through the aperture on the blade 300 (see FIGS. 3 and 4) (block 208). The graft may be secured by sutures based through the original hole drilled at the beginning of the procedure, facilitating passage of the bone plug 302. The doctor then slices anteriorly up the quadriceps tendon 126 underneath the skin of the patient (block 210). When an appropriate length of the quadriceps tendon 126 has been cut, the doctor severs the distal end of the quadriceps tendon 126 (block 212). The doctor then removes the tendon (block 214) and closes the incision (block 216).

Figure 3:
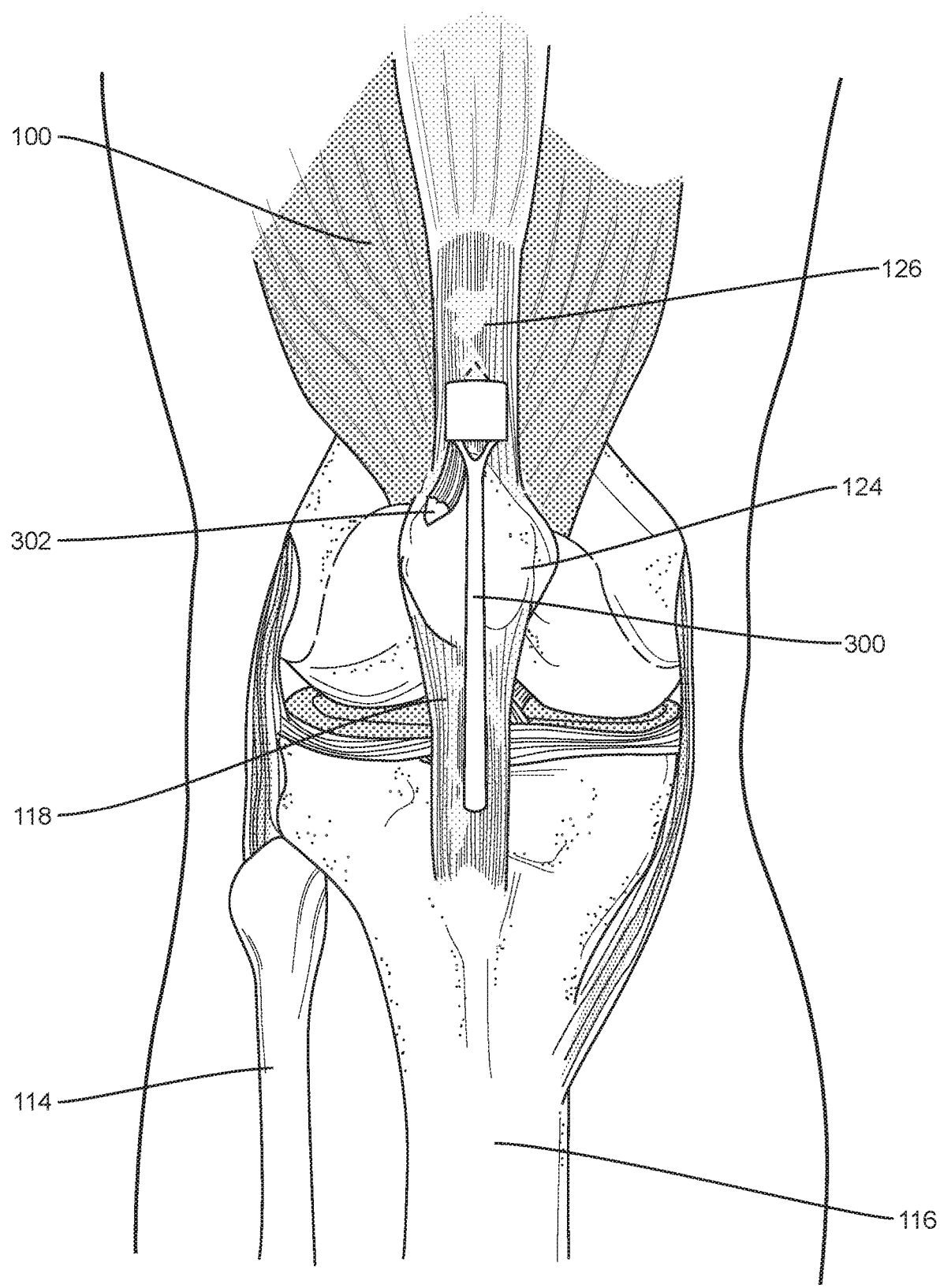
FIG. 3 illustrates a first view of a quadriceps tendon cutter harvesting a graft.
Figure 4:
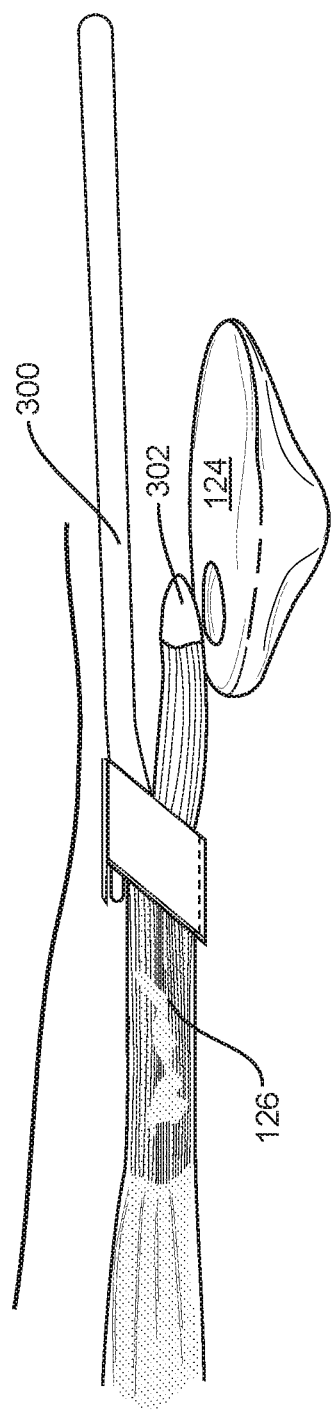
FIG. 4 illustrates a second view of a quadriceps tendon cutter harvesting a graft.

More details on the tendon cutting blade 300 and devices to sever the distal end of the quadriceps tendon 126 may be found in the patents referenced in the background and are not central to the present disclosure. However, FIGS. 3 and 4 show a v-shaped blade 300 cutting the quadriceps tendon 126 anteriorly up the quadriceps tendon 126 corresponding to block 210 of the process of FIG. 2. In particular, a bone plug or spur 302 is illustrated removed from the patella 124. Creation of this bone spur 302 is a result of use of the guide 500 illustrated in FIGS. 5-8.

In this regard, the guide 500 includes a handle portion formed from a body 502 that may be sized in a longitudinal direction (Lo) to accommodate a typical human hand to facilitate grasping thereof. The lateral direction (La) is discussed more below. The body 502 may further include a top central arcuate portion 504 and a bottom central arcuate portion 506 that are terminated by distal ridges 508(1)-508(2) on the top and distal ridges 510(1)-510(2) on the bottom. The distal ridges 508(1)-508(2) and 510(1)-510(2) assist in providing a handle shape to the body 502 to assist in manipulation of the guide 500. The body 502 may be made from a material such as polycarbonate or metal such as stainless surgical steel.

On either end of the body 502, a terminal portion 512(1)-512(2) (generically terminal portion 512) is positioned such that the terminal portion 512 extends from the handle portion formed by the body 502. The terminal portion 512 may be formed from a material such as polycarbonate or metal such as stainless surgical steel, and may be integrally formed with the body 502 or attached thereto through conventional means. Each terminal portion 512 may include a post 514 on a bottom side. The post 514 may be cylindrical, having a diameter of 2 mm and a height of 4 mm, for example. In an exemplary aspect, the terminal portion 512(1) may have a lateral (La) dimension of 10 mm, and the terminal portion 512(2) may have a lateral dimension of 11 mm. This lateral dimension corresponds to a width of the graft being cut from the tendon. While 10 mm and 11 mm are specifically contemplated, other guides could have different dimensions (e.g., 9 and 12 mm or 8 and 13 mm). While the example has the terminal portions 512 sized 1 mm differently, the present disclosure is not so limited. Thus, one end could be 10 mm and the other end 12 mm or some other variation. Further note that while illustrated as having two operational ends, the present disclosure is not so limited. Thus, for example, a tool with a single terminal portion 512 is within the scope of the present disclosure. Likewise, while perhaps unwieldy, three, four, or five terminal portions may be assembled in a star topology. It should be appreciated that the number and lateral dimensions of the terminal portions 512 may be selected to give doctors flexibility in use of the tool for creating different sized grafts. However, plural single-ended tools would provide the same flexibility, albeit perhaps at greater cost. It should be appreciated that other materials could be used so long as they are suitably resistant to cutting or chipping by a bone saw as described below with reference to FIGS. 9-10G.

With continued reference to FIGS. 5-8, the terminal portion 512 includes a first portion 516 and a generally u or v-shaped portion 518. The v-shaped portion 518 includes a first downwardly sloping wall 520, a flat portion or bottom wall 522, and a second upwardly sloping wall 524. The bottom wall 522 is generally parallel to the first portion 516. The lateral width of the terminal portion 512 helps determine a width of a bone plug or bone spur created from the patella and thus also helps determine a width of a harvested graft because the width of the bone plug typically corresponds closely to a width of the graft created. The upwardly sloping wall 524 may be about 6 mm long and more specifically 6.1 mm long. The longitudinal length of the bottom wall 522 may be about 10 mm. Likewise, the slope of the second upwardly sloping wall 524 is used to guide a bone saw into creating a cut at a desired angle as dictated by the angle of the upwardly sloping wall 524. In an exemplary aspect, the angle 526 is thirty degrees (30°). This will create, as explained below, a sixty degree (60°) angle in the bone spur such that the bone spur can be approximately an equilateral triangle. That is, the bone saw is held against the upwardly sloping wall 524 as cuts are made into the patella, thus creating a desired angle of cut.

Figure 9:
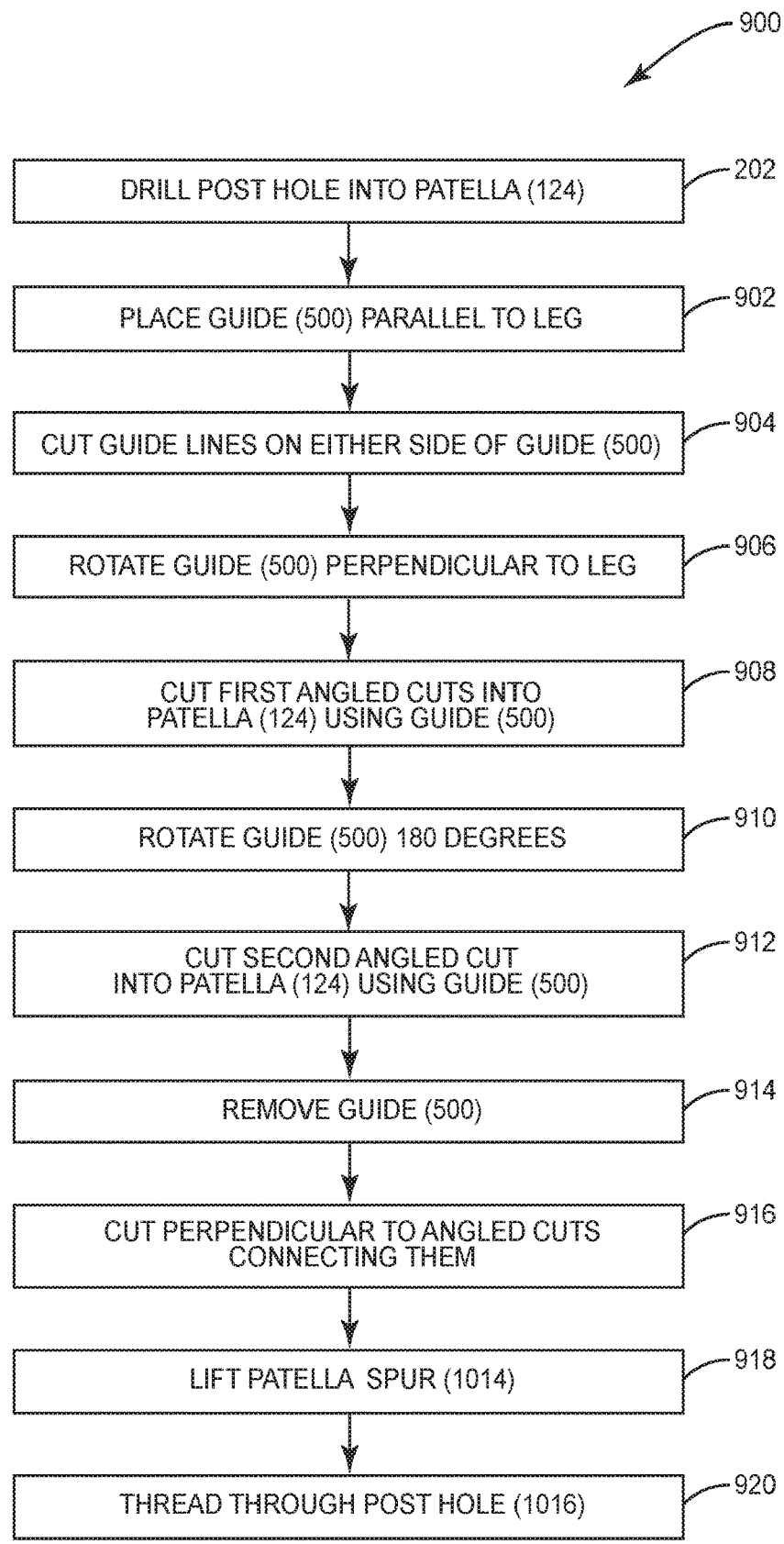
FIG. 9 illustrates a flowchart describing the process of using the cutting guide of FIG. 5.
Figure 10A:
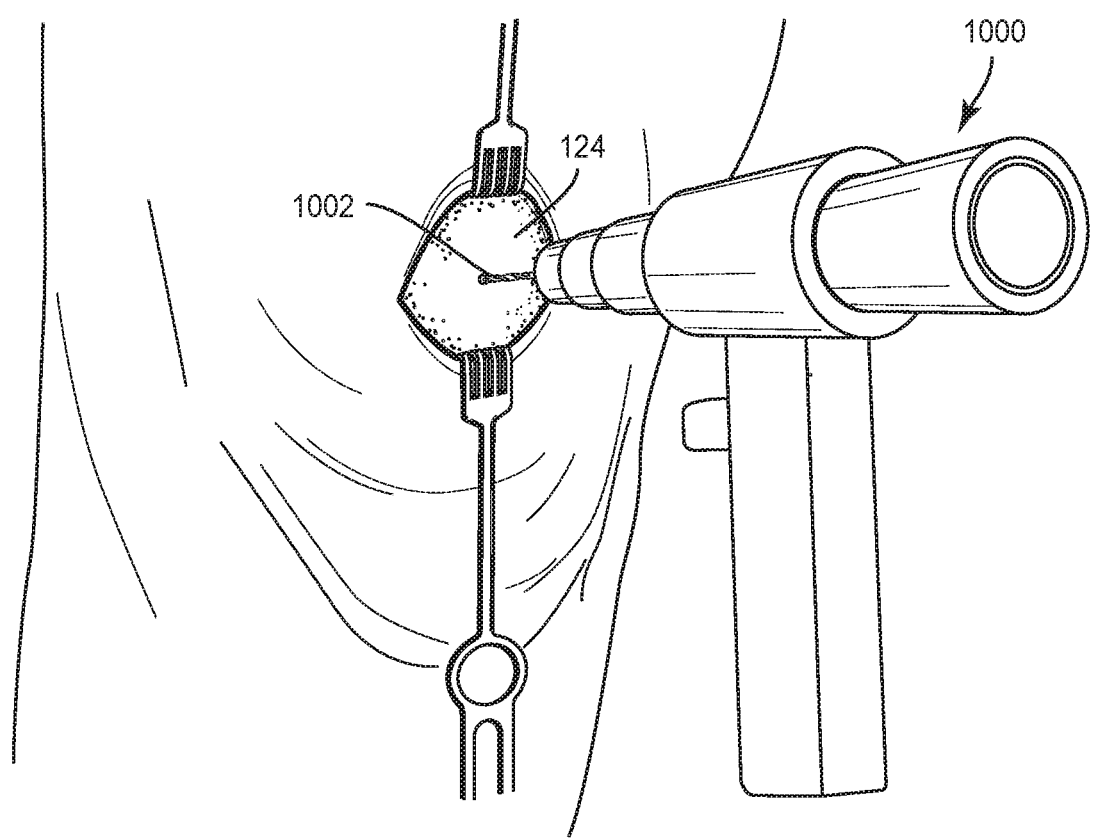
FIGS. 10A-10G illustrate exemplary steps from the process set forth in FIG. 9.
Figure 10B:
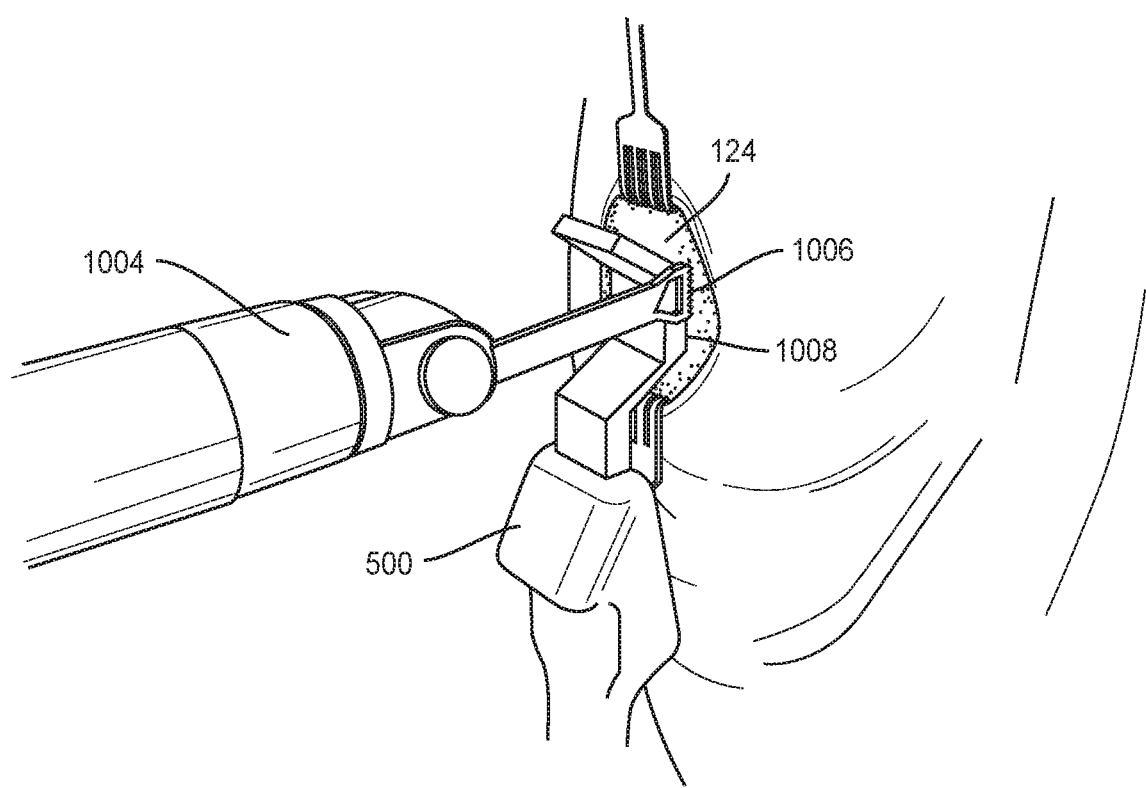
Figure 10C:
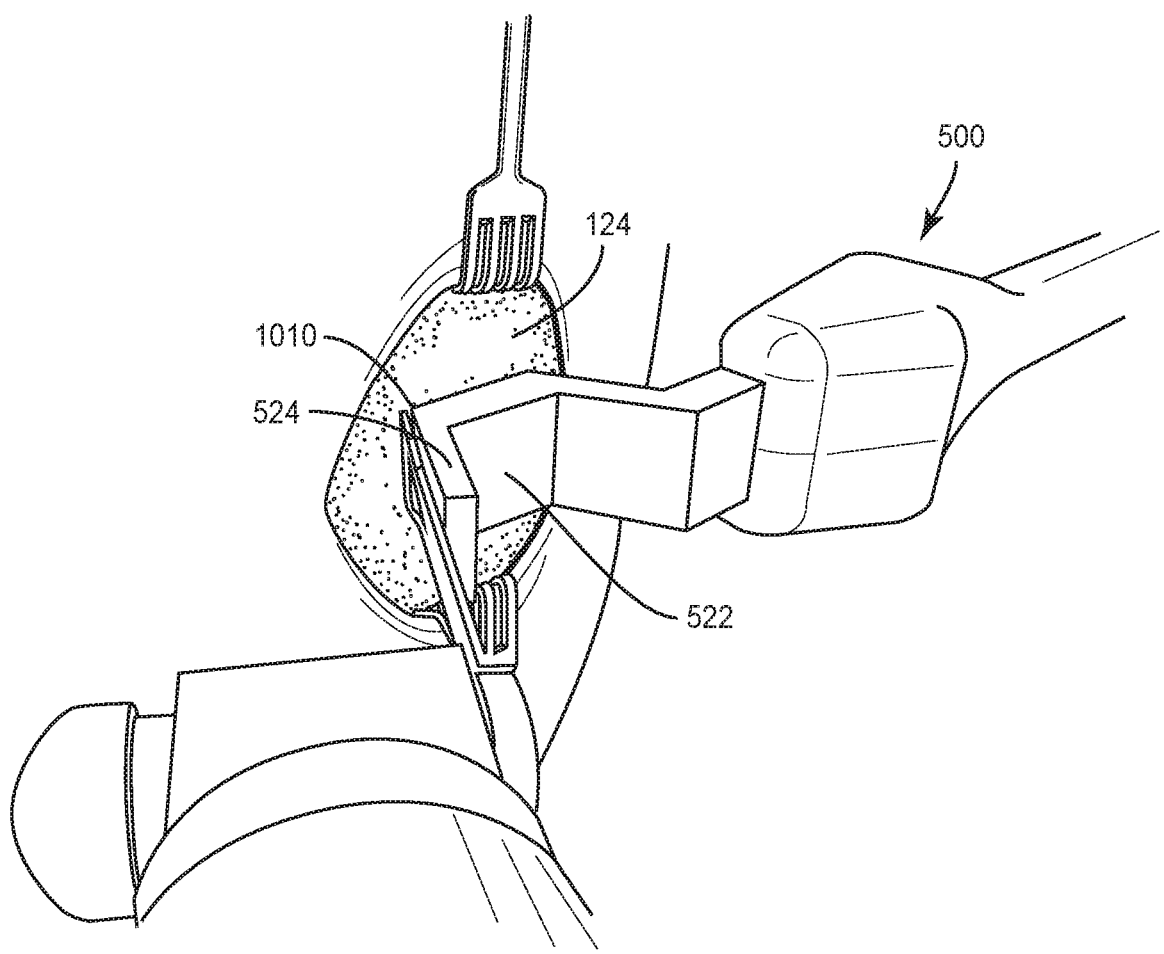
Figure 10D:
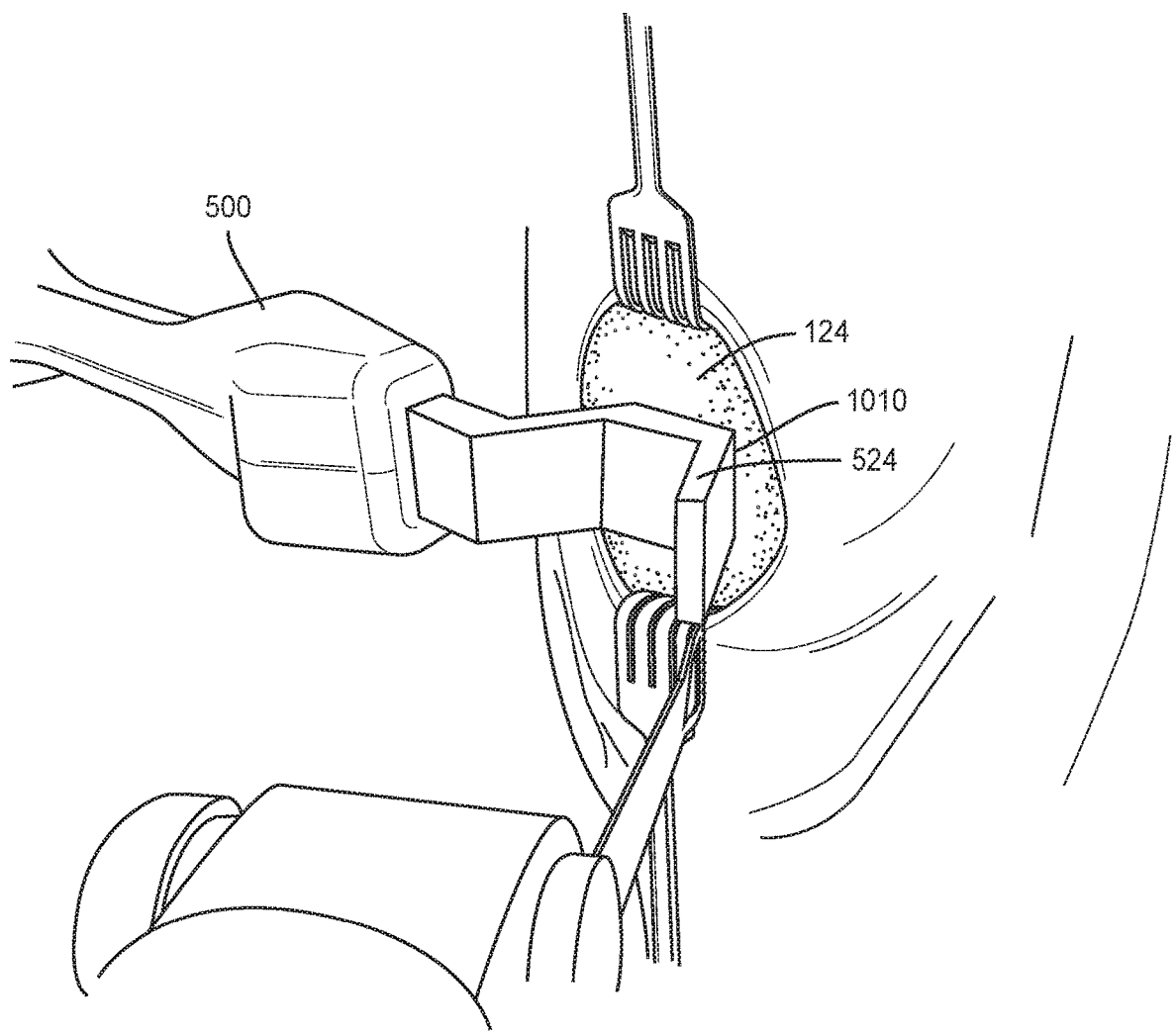
Figure 10E:
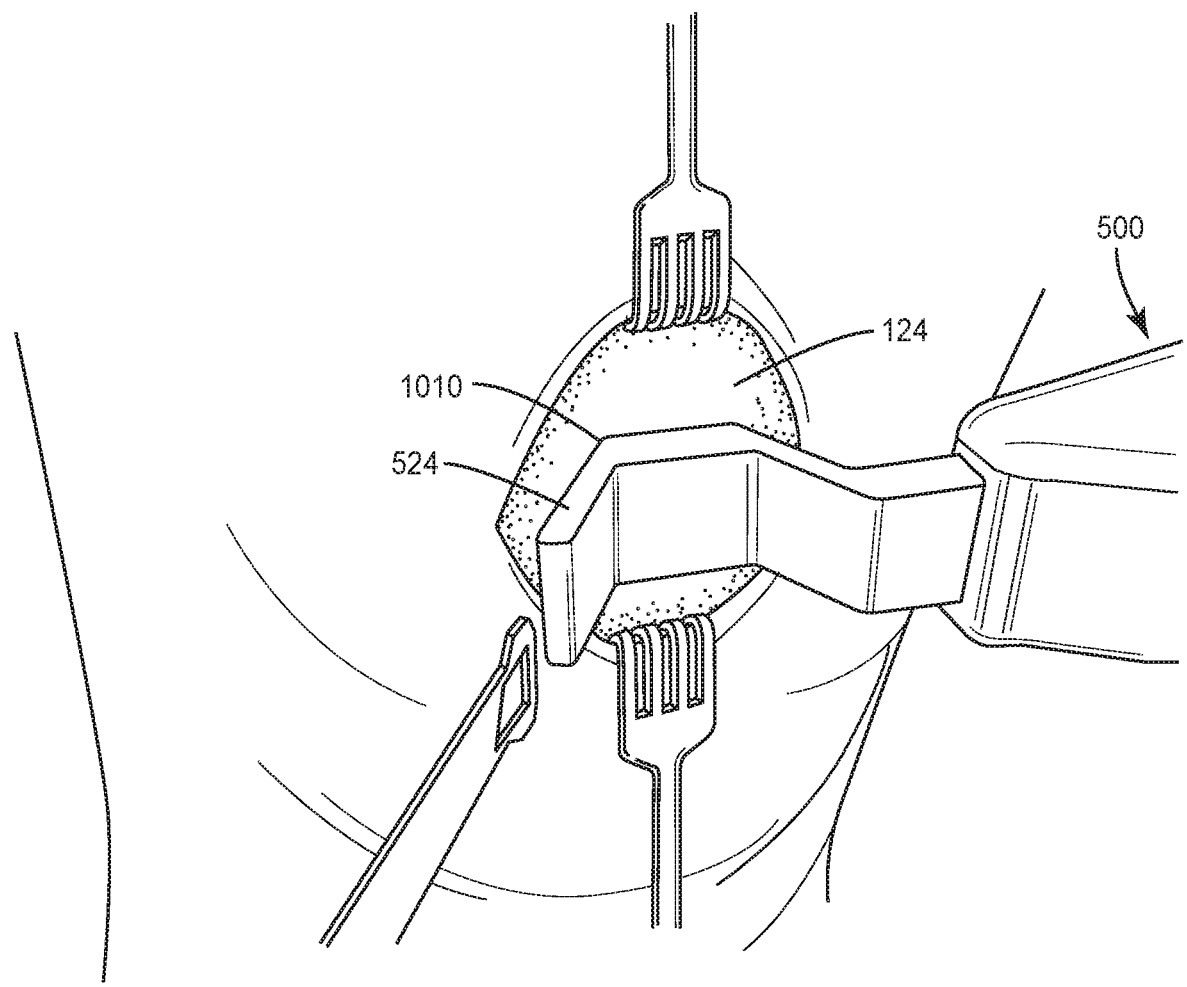
Figure 10F:
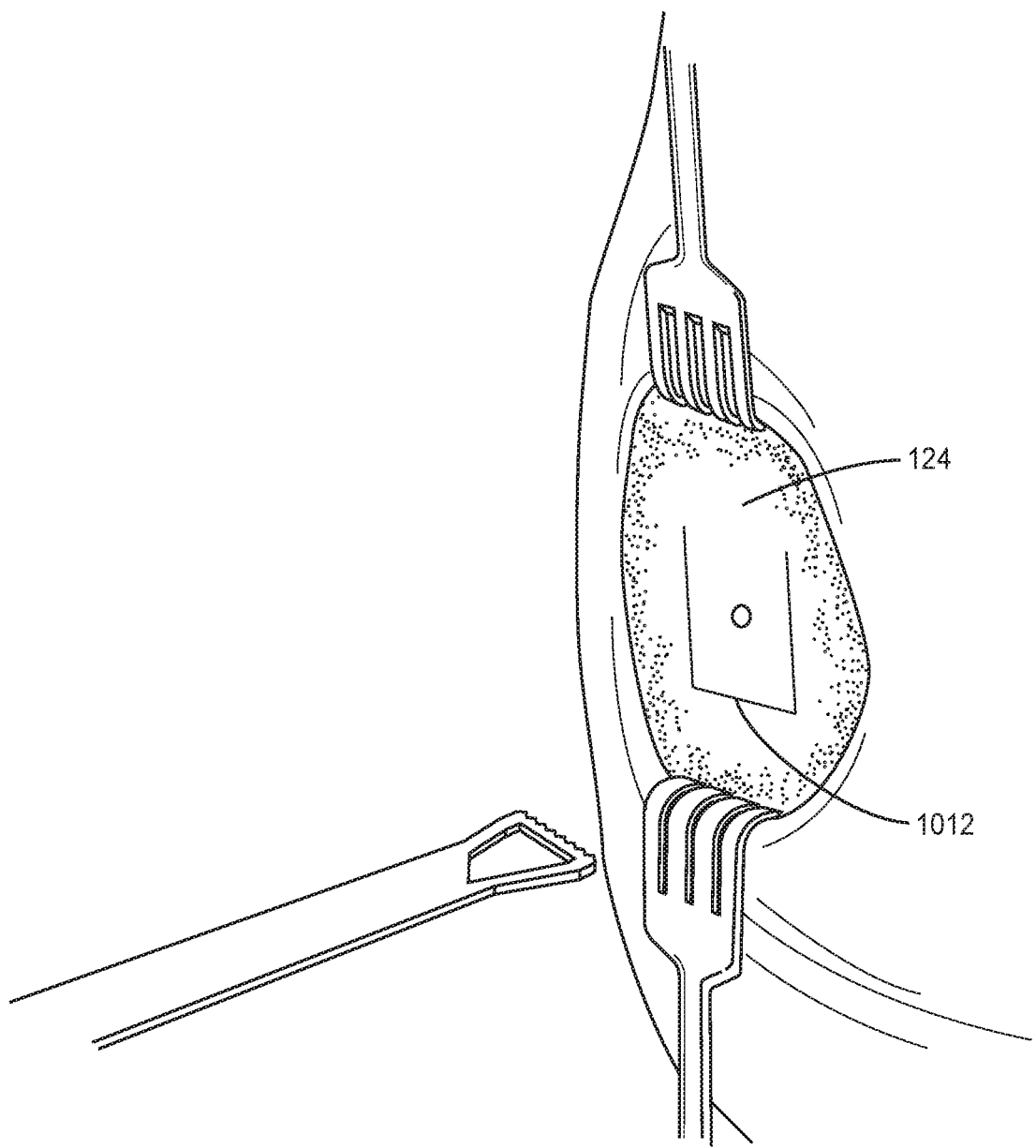
Figure 10G:
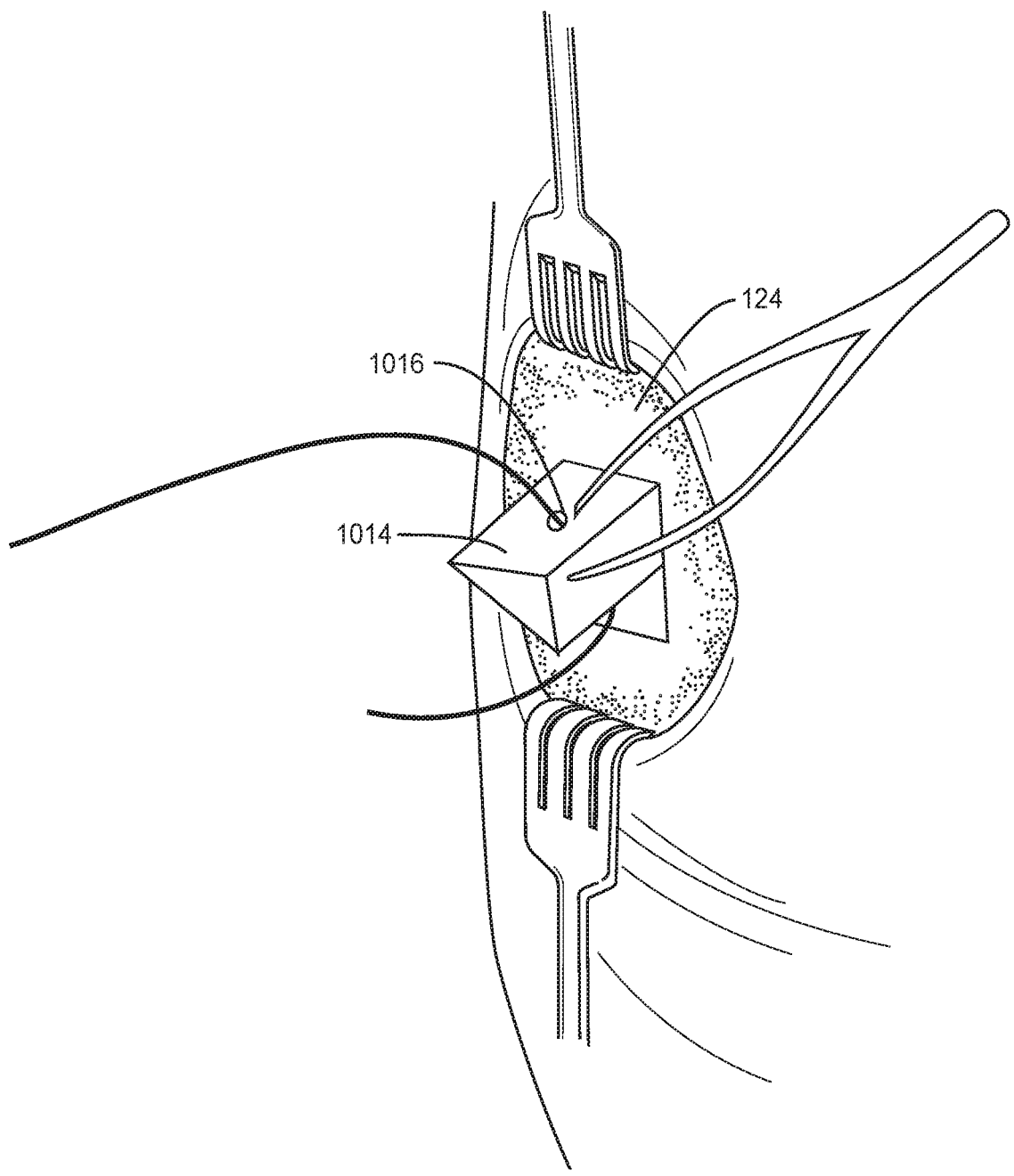

FIG. 9 illustrates a flow chart of a process 900 that expands on the steps in blocks 204, 206, and 208 of FIG. 2 to explain use of the guide 500. In particular, the process 900 starts (as illustrated) when the surgeon drills a post hole into the patella 124 (block 202). See FIG. 10A where a drill 1000 is used with a drill bit 1002 to form the post hole. The doctor then places the guide 500 parallel to the leg (in this context, longitudinal direction Lo parallel to the longitudinal length of the femur) (block 902). The doctor then cuts guide lines on either side of the guide 500 (block 904). See FIG. 10B where a reciprocating bone saw 1004 has a blade 1006 pressed against the side 1008 of the guide 500 to score the patella 124. Note that such guide lines are formed on both sides of the guide 500. The doctor then rotates the guide 500 perpendicular to the leg (block 906). A bone saw (which may be the bone saw 1004 or a different saw) is then used to cut first angled cuts into the patella 124 using the guide 500 (block 908). Since the angle 526 is 30°, the angle of the bone spur will be 60°. See FIG. 10C, where the saw is placed against the second upwardly sloping wall 524 and the angle thereof forms the angle of the cut. A distal corner 1010 is formed at the intersection of the flat portion of the bottom wall 522 and the upwardly sloping wall 524. Note that the corner 1010 of the upwardly sloping wall 524 is positioned on the guide line formed at block 904. The doctor then rotates the guide 500 one hundred eighty degrees (block 910) so that the upwardly sloping wall 524 is on the other guide line formed at block 904. See FIG. 10D. The doctor then uses the saw to cut a second angled cut into the patella 124 using the guide 500 (block 912). Specifically, the upwardly sloping wall 524 directs the blade of the saw to the guide line and forms the cut at the desired location as shown in FIG. 10E. Again, since the angle 526 is 30°, the angle of the bone spur will be 60°, thereby forming something close to an equilateral triangle of cut bone. The doctor then removes the guide 500 (block 914) to expose the cuts on the patella 124. The doctor then uses the saw to cut perpendicular to the angled cuts, thereby connecting them (block 916) as shown by cut 1012 in FIG. 10F. The doctor then lifts the patella spur 1014 (block 918) using forceps or the like. The doctor may place a thread through the post hole 1016 (block 920) as shown in FIG. 10G.

While much of the process 900 is described as a doctor performing the steps, it is possible that such actions may be performed by robotic arms controlled by a person or a computer.

What is claimed is:

1. A cutting guide, comprising:
   an elongated handle portion comprising a primary longitudinal axis extending between a first end and a second end, the elongated handle portion sized to be grasped by a human hand; and
   a terminal portion extending generally along the primary longitudinal axis, but at an angle thereto from the first end of the elongated handle portion, the terminal portion comprising:
      a flat portion extending away from the first end of the elongated handle portion generally along the primary longitudinal axis, but at an angle thereto, the flat portion having a bottom side and a corner spaced from the first end of the elongated handle portion;
      a post extending from the bottom side perpendicular to the flat portion; and
      an upwardly sloping wall configured to act as a saw guide, the upwardly sloping wall extending upwardly from the corner and wherein the post extends from the flat portion in a first direction and the upwardly sloping wall extends from the flat portion in a second direction generally opposite the first direction.

2. The cutting guide of claim 1, wherein the terminal portion further comprises a downwardly sloping wall between the flat portion and the elongated handle portion.

3. The cutting guide of claim 1, wherein the terminal portion comprises a polycarbonate or metal terminal portion.

4. The cutting guide of claim 1, further comprising:
   a second terminal portion extending along the primary longitudinal axis from the second end of the elongated handle portion, the second terminal portion comprising:
      a second flat portion extending away from the second end of the elongated handle portion along the primary longitudinal axis, the second flat portion having a second bottom side and a second corner spaced from the second end of the elongated handle portion;
      a second post extending from the second bottom side; and
      a second upwardly sloping wall configured to act as a saw guide, the second upwardly sloping wall extending upwardly from the second corner.

5. The cutting guide of claim 1, wherein the terminal portion comprises a lateral width of ten or eleven millimeters (10 or 11 mm).

6. The cutting guide of claim 1, wherein the corner forms an angle of 30 degrees.

7. The cutting guide of claim 1, wherein the elongated handle portion comprises an arcuate portion.

8. The cutting guide of claim 1, wherein the post is cylindrical having a diameter of 2 mm and a height of 4 mm.

9. The cutting guide of claim 1, wherein the upwardly sloping wall has a length of 6.1 mm.

10. The cutting guide of claim 1, wherein the flat portion has a length of 10 mm.

* * * * *